(12) United States Patent
Wu et al.

(10) Patent No.: US 10,183,909 B2
(45) Date of Patent: Jan. 22, 2019

(54) PROCESS FOR PREPARATION OF N-BOC BIPHENYL ALANINOL

(71) Applicants: CHIRAL QUEST (SUZHOU) CO., LTD., Jiangsu (CN); JIANGXI LONG LIFE BIO-PHARMACEUTICAL CO., LTD., Jiangxi (CN)

(72) Inventors: Shengwen Wu, Jiangsu (CN); Wenge Li, Jiangsu (CN); Lei Wu, Jiangsu (CN); Li Zou, Jiangsu (CN); Siming Hu, Jiangsu (CN); Tengyue Xu, Jiangsu (CN); Hongfeng Liu, Jiangsu (CN); Yi Tao, Jiangsu (CN); Yongxiang Chi, Jiangsu (CN)

(73) Assignees: CHIRAL QUEST (SUZHOU) CO., LTD., Jiangsu (CN); JIANGXI LONG LIFE BIO-PHARMACEUTICAL CO., LTD., Jiangxi (CN)

( * ) Notice: Subject to any disclaimer, the term of this patent is extended or adjusted under 35 U.S.C. 154(b) by 0 days.

(21) Appl. No.: 15/766,979

(22) PCT Filed: Sep. 9, 2016

(86) PCT No.: PCT/CN2016/098517
§ 371 (c)(1),
(2) Date: Apr. 9, 2018

(87) PCT Pub. No.: WO2017/059759
PCT Pub. Date: Apr. 13, 2017

(65) Prior Publication Data
US 2018/0297941 A1    Oct. 18, 2018

(30) Foreign Application Priority Data
Oct. 10, 2015 (CN) .......................... 2015 1 0654835

(51) Int. Cl.
| C07C 269/06 | (2006.01) |
| C07C 269/00 | (2006.01) |
| C07C 271/64 | (2006.01) |
| C07C 231/12 | (2006.01) |

(52) U.S. Cl.
CPC .......... *C07C 269/06* (2013.01); *C07C 231/12* (2013.01); *C07C 269/00* (2013.01); *C07C 271/64* (2013.01)

(58) Field of Classification Search
CPC ... C07C 269/06; C07C 271/64; C07C 269/00; C07C 231/12
See application file for complete search history.

(56) References Cited

U.S. PATENT DOCUMENTS

2015/0210632 A1    7/2015 Zhu et al.

FOREIGN PATENT DOCUMENTS

| CN | 105198775 A | 12/2015 |
| WO | WO-2008/138561 A1 | 11/2008 |
| WO | WO-2010/081410 A1 | 7/2010 |
| WO | WO-2011/073173 A1 | 6/2011 |
| WO | WO-2013/026773 A1 | 2/2013 |
| WO | WO-2014/032627 A1 | 3/2014 |
| WO | WO-2014/152835 A1 | 9/2014 |
| WO | WO-2015/024991 A1 | 2/2015 |
| WO | WO2015024991 | * 2/2015 |
| WO | WO-2015/037460 A1 | 3/2015 |

OTHER PUBLICATIONS

Carlier et al. (Catalytic Asymmetric Synthesis of Protected Tryptophan Regioisomers, J. Org. Chem., 67, 6256-6259, published 2002) (Year: 2002).*
International Search Report and Written Opinion issued in corresponding application No. PCT/CN2016/098517 dated Dec. 21, 2016, 11 pages.
Fox, Martin E. et al. " Large-Scale Synthesis of a Substituted D-Phenylalanine Using Asymmetric Hydrogenation" Organic Process Research & Development, vol. 15, Aug. 5, 2011 ISSN:1520-586X, pp. 1163-1171.

(Continued)

*Primary Examiner* — Yevgeny Valenrod
*Assistant Examiner* — Blaine G Doletski
(74) *Attorney, Agent, or Firm* — Foley & Lardner LLP; Tianran Yan

(57) ABSTRACT

A process is provided for preparation of (R)-N-Boc biphenyl alaninol. It provides a preparation process for a compound outlined as compound 4, which includes these operations: in one of the alcohol solvents, asymmetric hydrogenation of 5 in the presence of [Rh(Duanphos)(X)]Y and hydrogen to provide compound 4. Here "Duanphos" is (Rc,Sp)-Duanphos or (Sc,Rp)-Duanphos; X is NBD or/and COD; Y is one or more of BF4, PF6, SbF6. This process has a lot of advantages, such as low cost, safe operation, less pollution and high yield. The product was obtained in >99% purity and ee which is suitable to scale up in industrial scale.

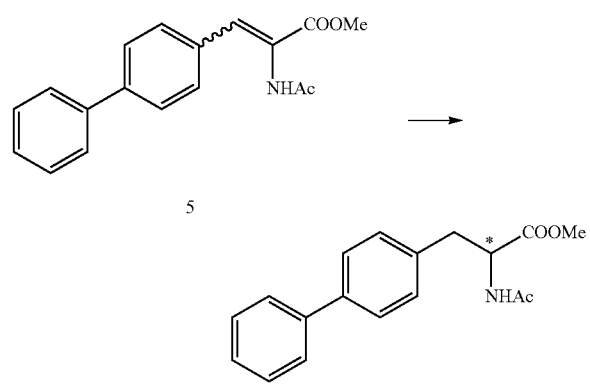

17 Claims, No Drawings

(56) References Cited

OTHER PUBLICATIONS

Gallou-Dagommer, Isabelle et al. "Asymmetric Synthesis of Functionalized 1,2,3,4-Tetrahyfroquinolines" Organic Letters, vol. 3, No. 13, Jun. 2, 2001, ISSN:1523-7052, pp. 1163-1171.
First Office Action issued in the priority application CN201510654835.3 (CN 105198775) dated Jul. 12, 2016 with its English translation, 13 pages.
Second Office Action issued in the priority application CN201510654835.3 (CN 105198775) dated Mar. 13, 2017 with its English translation, 10 pages.
Mohar, Barbara et al. "Practical Enantioselective Hydrogenation of a-Aryl-and a-Carboxyamidoethylenes by Practical Enantioselective Hydrogenation of a-Aryl-and a-Carboxyamidoethylenes by Rhodium(I)-{1, 2-Bis[(o-tertbutoxyphenyl)(phenyl)phosphine]ethane}" Adv. Synth. Catal., vol. 355, Jan. 16, 2013, ISSN:1615-4169, pp. 594-600.
European Patent Office. Extended European Search Report dated Aug. 22, 2018. European Patent Application No. 16853064.0-1109 / 3359522. International Patent Application No. PCT/CN2016/098517. Name of Applicant: Chiral Quest (suzhou) Co., Ltd., et al. English Language. 8 pages.

\* cited by examiner

PROCESS FOR PREPARATION OF N-BOC BIPHENYL ALANINOL

CROSS REFERENCE TO RELATED APPLICATION

The present application claims priority of Chinese Patent Application 201510654835.3, filed Oct. 10, 2015, the contents of which are incorporated herein by reference in their entireties.

FIELD OF INVENTION

The invention relates to a preparation process for N-Bocbiphenyl alaninol.

PRIOR ARTS

The U.S. Food and Drug Administration recently approved Entresto (sacubitril/valsartan) tablets for the treatment of NYHA II-IV heart failure. It acts to enhance the protective neurohormonal systems of the heart (NP system) while simultaneously suppressing the harmful system. The drug has been shown to reduce the rate of cardiovascular death and hospitalization related to heart failure. A few synthetic routes to Entresto had been published and most of them use (R)-N-Bocbiphenyl alaninol as a key intermediate. Therefore people developed many synthetic routes and process for preparation of (R)-N-Boc biphenyl alaninol.

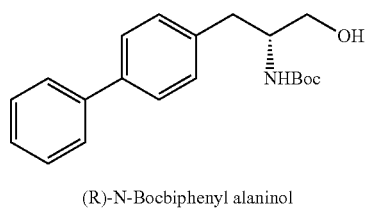 [SMILES: CC(C)(C)OC(=O)N[C@@H](CO)Cc1ccc(-c2ccccc2)cc1]

(R)-N-Bocbiphenyl alaninol

In early stage classic resolution was used to obtain desired configuration. For example WO2010/081410 related to preparation of 2-acetylamino-3-biphenyl propanoic acid. It was then converted to (R)-N-acetyl biphenyl alanine which was converted to (R)-N-Boc biphenyl ananiol by a series of chemical transformations.

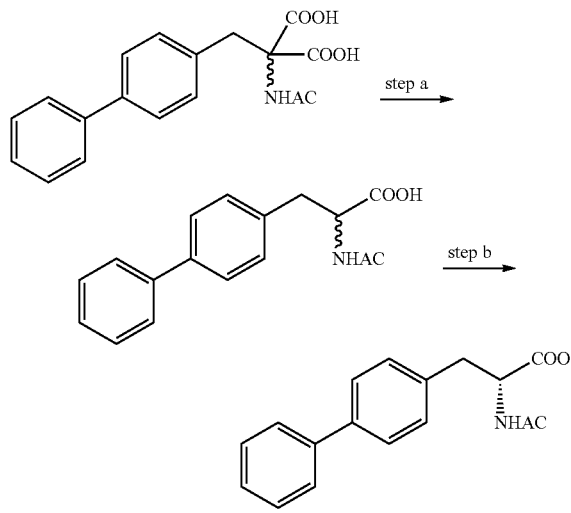

A drawback of this process is that the acetyl group is removed under the reaction conditions of the first step and thus a further chemical step is necessary in order to reintroduce it. Then its enantiomerically pure 2-acylamino-3-biphenyl propanoic acid was obtained by resolution of the racemates, e.g. by salt formation with a chiral amine, or by enzymatic resolution. Due to wasting of the undesired enantiomer or complicated process to racemize it, the cost of resolution approach is usually higher than one employing chiral pool or asymmetric technology.

WO2014/032627 related a new approach using chiral epihalohydrin reacting with Grinard reagent. This process first provide optical active chloride alcohol which then react with amide under Mitsnuobu conditions to afford chiral amine with desired configuration by reversed replacement. Then hydrolysis and Bocylation provide target compound. This route employs chrial pool and with shorter steps. However the final product is difficulty to purify due to by-product accompanied with Mitsunobu reaction.

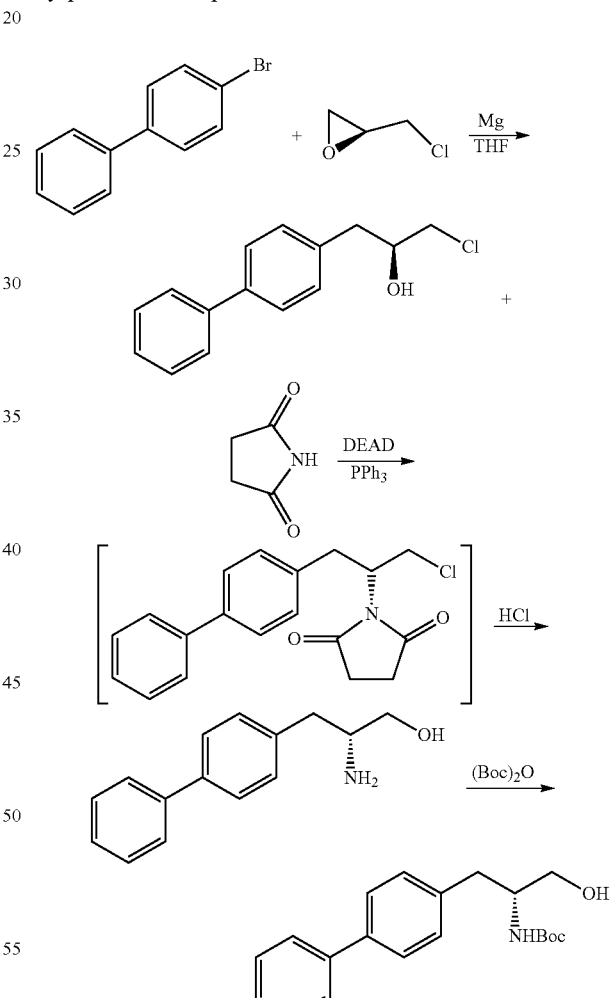

WO2013/026773 described a synthesis of R-biphenyl alaninol starting from biphenyl aldehyde and outlined as below. The advantages of this route are short and established chiral center efficiently by asymmetric hydrogenation. It provided the intermediates with high optical purity. However the process used too much catalyst for asymmetric hydrogenation and need additional Pd/C catalyst to remove benzyl group. In addition it reduced ester and amide simultaneous using lot of lithium aluminum hydride which makes the route with ecological and safety disadvantages. Furthermore, N-deprotection of 4 needs additional higher pressure equipment.

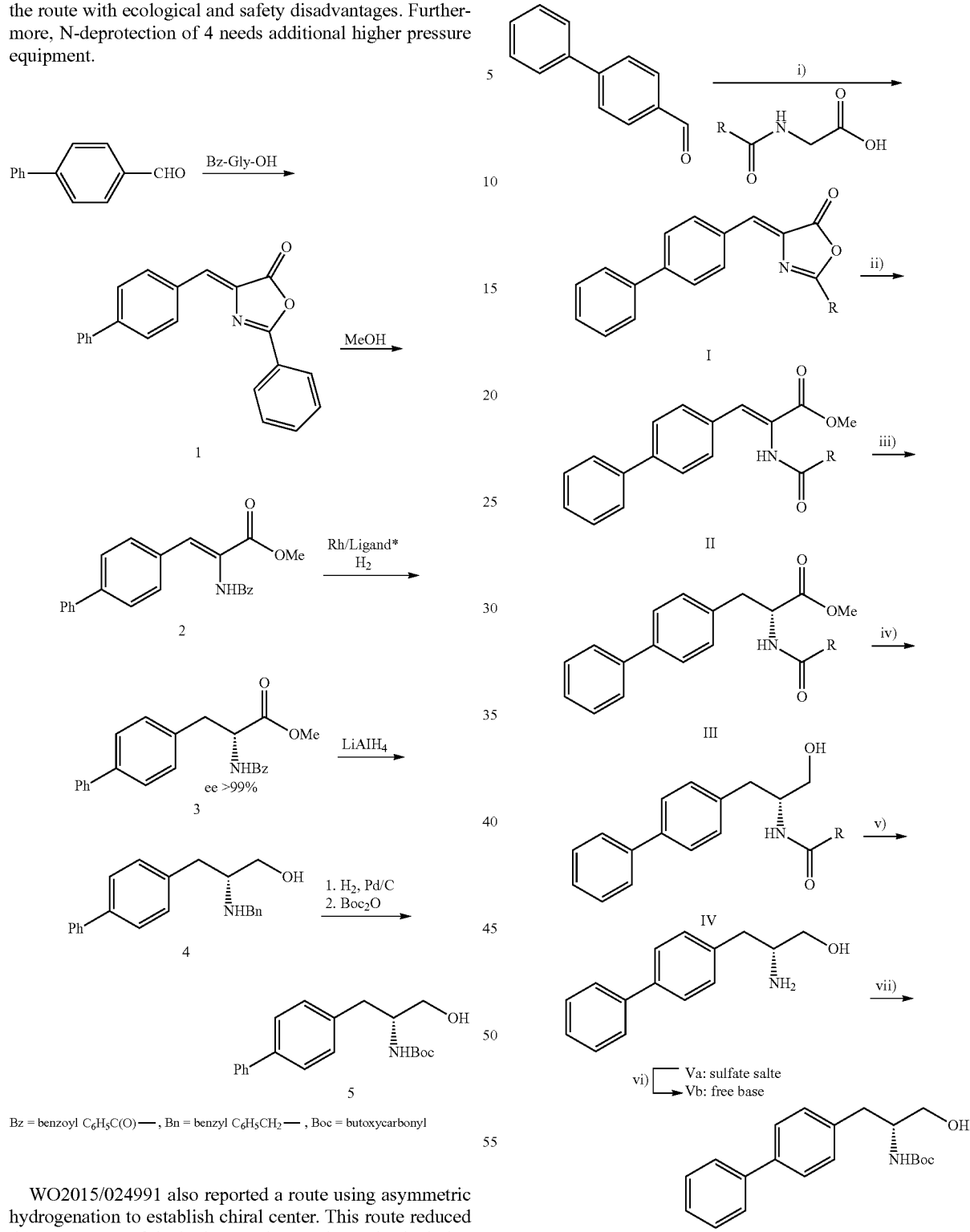

Bz = benzoyl C₆H₅C(O)—, Bn = benzyl C₆H₅CH₂—, Boc = butoxycarbonyl

WO2015/024991 also reported a route using asymmetric hydrogenation to establish chiral center. This route reduced the ester group of the hydrogenation product selectively but did not attack that amide group. Under suitable conditions, NaBH₄ reduced the ester to corresponding alcohol. The highlight of this route is that it employs sulfuric acid to do hydrolysis of amide rather than hydrochloride acid which is commonly used. The purity of its key intermediate was enriched by forming sulfuric acid salt. Then protection with Boc anhydride provide target compound.

i) Ac₂O, EtOAc, KOAc; ii) NaOMe, MeOH; iii) Rh(I)/L', H₂; iv) NaBH₄, THF; v) aq. H₂SO₄, vi) aq. NaOH, toluene/THF; vii) Boc₂O, toluene/THF/heptanes
R = methyl, phenyl; Boc = butoxycarbonyl; THF = tetrahydrofuran; L' = ligand There are a few reports for preparation of (S)-N-Boc biphenyl alaninol by reduction of its corresponding N-Boc amino acid. For instance, WO2008/138561 reported reduction of (S)-N-Boc biphenyl alanine by sodium borohydride to afford its alcohol outlined as below. However there is no report about reduction of (R)-N-Boc biphenyl alanine or its ester to afford corresponding R-N-Boc biphenyl alaninol.

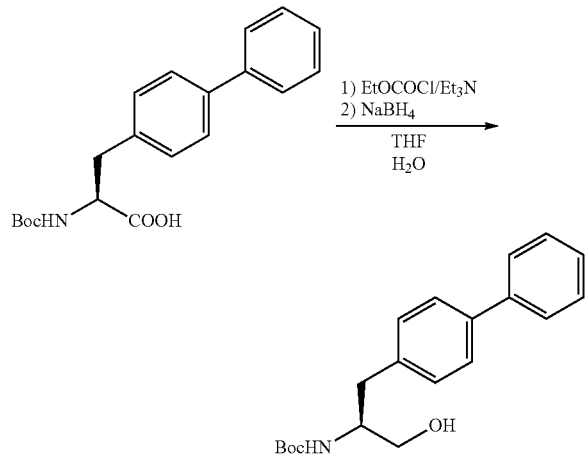

There are different disadvantages for those reported routes, e.g. safety or ecological issue. Therefore there is a need to develop inexpensive, safer and environmentally benign process to prepare (R)-N-Boc biphenyl alaninol.

Content of the Present Invention

To overcome the abovementioned drawbacks from existing process such as higher cost and using dangerous reducing reagents, the present invention aims to provide a process with reduced cost and safer operations, less pollution and high yield. It produce the product in >99% purity and ee which is suitable to scale up in industrial scale.

This invention provides a preparation process for a compound outlined as compound 4, which includes these operations: in one of the alcohol solvents, asymmetric hydrogenation of 5 in the presence of [Rh(Duanphos)(X)]Y and hydrogen to provide compound 4. Here "Duanphos" is (Rc,Sp)-Duanphos or (Sc,Rp)-Duanphos; X is NBD or/and COD; Y is one or more of BF4, PF6, SbF6.

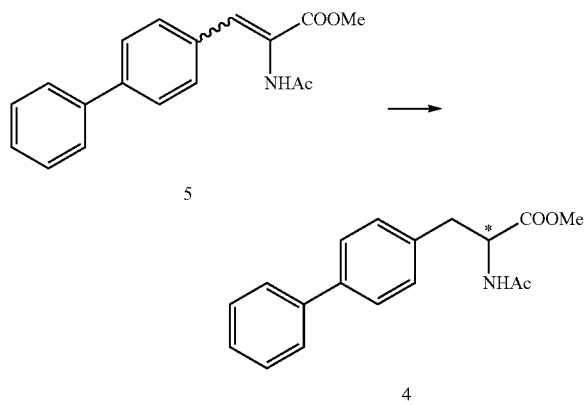

Here, ∼ indicates that compound 5 is E or/and Z; * indicates that compound 4 has a chiral center, which will be R configuration when (Rc,Sp)-Duanphos is used. Otherwise it will be S configuration when (Sc,Rp)-Duanphos is used.

In one embodiment of the preparation of compound 4, the pressure of hydrogen was in the regular range of this application (for instance 0.1~0.5 MPa), but preferred to be 0.5~3.0 MPa, e.g. 1.5~2.0 MPa. It was relative pressure.

In one embodiment of the preparation of compound 4, the solvent was the common alcohols for this application, and preferred one was methanol.

In another preferred embodiment of the preparation of compound 4, the ratio of the alcohol solvent to the mole of the substrate was in the regular range of this kind of transformation, e.g. 1~10 L/mol; preferred to be 1.5~3 L/mol, e.g. 2.3~2.8 L/mol.

In the preparation of compound 4, the structure of described (Rc,Sp)-Duanphos is:

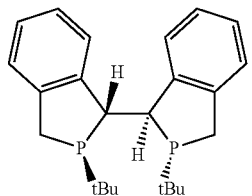 [SMILES: CC(C)(C)[P@@]1Cc2ccccc2[C@@H]1[C@H]1c2ccccc2C[P@]1C(C)(C)C]

In the preparation of compound 4, the structure of described (Sc,Rp)-Duanphos is:

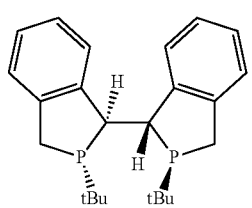 [SMILES: CC(C)(C)[P@]1Cc2ccccc2[C@H]1[C@@H]1c2ccccc2C[P@@]1C(C)(C)C]

In one embodiment of the preparation of compound 4, the described X preferred to be NBD.

In the preparation of compound 4, the described NBD is bicycle[2.2.1]hepta-2,5-diene.

In the preparation of compound 4, the described COD is 1, 5-cyclooctandiene.

In one embodiment of the preparation of compound 4, the described Y preferred to be BF4.

In one embodiment of the preparation of compound 4, the mole ratio of [Rh(Duanphos)(X)]Y to substrate 5 was in the regular range of this kind of transformation, e.g. 0.00001~0.01, but preferred to be 0.0001~0.0003, e.g. 0.00025~0.000265.

In one embodiment of the preparation of compound 4, the hydrogenation temperature was in the regular range of this transformation, preferred to be 0~60° C., and the best range was 20~30° C.

In the preparation of compound 4, the completeness of the reaction can be monitored by regular methods in this area, such as TLC, HPLC or NMR. In general compound 5 stopped to react was regarded as the end point. The reaction time usually is 1~20 h, better in 4~8 h.

The preparation process for described compound 4 includes following step too: in organic solvent, compound 6 condensed with compound 7 in the presence of base to afford compound 5. It is outlined as:

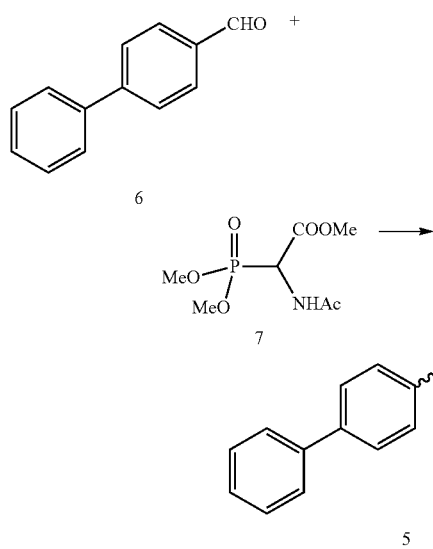

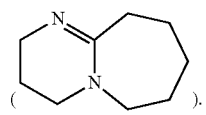

and DBU is the preferred one.

In the preparation of compound 5, the mole ratio of selected base to compound 7 can be in the regular range used for this transformation. It preferred in the range of 1.0~3.0, better 1.1~2.0, e.g. 1.2~1.6.

In the preparation of compound 5, the mole ratio of compound 6 to compound 7 can be in the regular range used for this transformation. It preferred in the range of 1.0~4.0, e.g. 1.1~2.0.

In one embodiment of the preparation of compound 5, the reaction temperature for condensation was in the regular range of this transformation, preferred to be 0~40° C., and the best range was 10~25° C.

In the preparation of compound 5, the completeness of the condensation reaction can be monitored by regular methods in this area, such as TLC, HPLC or NMR. In general compound 7 stopped to react was regarded as the end point. The reaction time usually is 1~10 h, better in 2~8 h, e.g. 4~6 h.

The present invention also provided a preparation process for compound 3, which include following steps:

(1) Prepare compound 4 according to process described above.

(2) In the presence of base, compound 4 react with di-tertbutyl dicarbonate to form amide compound 3.

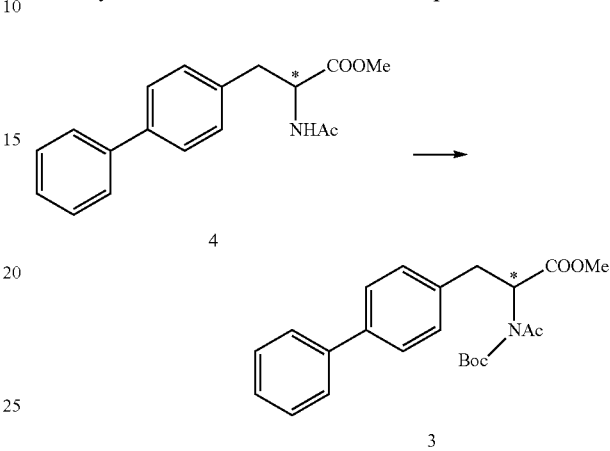

Here * indicates that compound 4 and compound 3 have chiral centers in their molecular structure. 4 and 3 have same configuration R or S.

In the above second step (2) process, the reaction solvents can be common ones usually used in this transformation. In one embodiment the solvents can be one of haloalkanes, nitriles, alcohols, ethers, pyridine and NMP, or any combinations of them. In other preferred embodiments, the haloalkanes can be dichloromethane, and the nitriles can be acetonitrile. In other embodiments the alcohols can be common alcohol solvents used for this transformation and preferred one was methanol. In another embodiment the ether can be tetrahydrofuran.

In the above second step (2) process, the ratio of selected solvent to the mole of compound 4 was in the regular range of this kind of transformation, e.g. 1~6 L/mol; preferred to be 2~3 L/mol.

In the above second step (2) process, the base is one of the common bases used for this transformation. It can be inorganic base or/and organic base. Inorganic base can be one of the common ones, e.g. sodium bicarbonate and or sodium carbonate. Organic base can be one of the common ones or any combinations of them (e.g. ammonia aqueous, morpholine, pyridine, triethyl amine, ethanol amine, ethylene diamine, 4-dimethylaminopyridine, diisopropyl ethyl amine), and preferred to be 4-dimethylaminopyridine.

In the above second step (2) process, the mole ratio of selected base to compound 4 can be in the regular range used for this transformation. It preferred to be in the range of 0.05~1.0, better 0.1~0.2, e.g. 0.12~0.18.

In the above second step (2) process, the mole ratio of di-tert-butyl dicarbonate to compound 4 can be in the regular range used for this transformation. It preferred to be in the range of 1.0~4.0, better 1.2~2.0, e.g. 1.5~1.8.

In the above second step (2) process, the reaction temperature for bocylation was in the regular range of this transformation, preferred to be 30~70° C., and it better to be 60~66° C.

In the above second step (2) process, the completeness of the bocylation can be monitored by regular methods in this area, such as TLC, HPLC or NMR. In general compound 4 stopped to react was regarded as the end point. The reaction time usually is 1~10 h, better in 3~7 h, e.g. 5~6 h.

The present invention also provided a preparation process for compound 2, which include following steps:
(a) Prepare compound 3 according to process described above.
(b) In organic solvent, compound 3 react with hydrazine to afford compound 2.

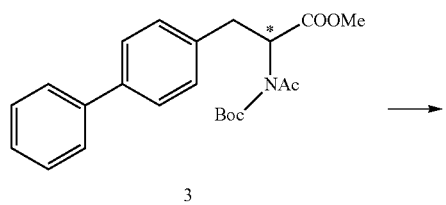

3

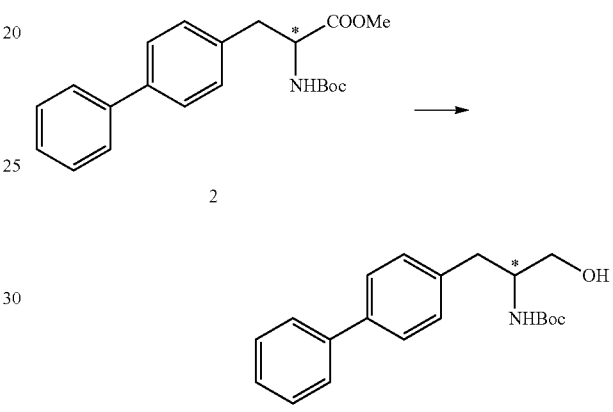

Here * indicates that compound 3 and compound 2 have chiral centers in their molecular structure. 3 and 2 have same configuration R or S.

In the above step (b) process, the reaction solvents can be common ones usually used in this transformation. In one embodiment the solvents can be one of haloalkanes, nitriles, alcohols, ethers, pyridine and NMP, or any combinations of them. In other preferred embodiments, the haloalkanes can be dichloromethane, and the nitriles can be acetonitrile. In other embodiments the alcohols can be common alcohol solvents used for this transformation and preferred one was methanol. In another embodiment the ether can be tetrahydrofuran.

In the above step (b) process, the ratio of selected solvent to the mole of compound 3 was in the regular range of this kind of transformation, e.g. 1~6 L/mol; preferred to be 2~3 L/mol.

In the above step (b) process, hydrazine and be added as hydrazine hydrate.

In the above step (b) process, the mole ratio of hydrazine to compound 3 can be in the regular range used for this transformation. It preferred to be in the range of 1~5, better 2~4, e.g. 2.8~3.5.

In the above step (b) process, the reaction temperature for hydroazinolysis was in the regular range of this transformation, preferred to be 0~40° C., and it better to be 0~20° C., e.g. 0~10° C.

In the above step (b) process, the completeness of the hydrazinolysis can be monitored by regular methods in this area, such as TLC, HPLC or NMR. In general compound 3 stopped to react was regarded as the end point. The reaction time usually is 1~20 h, better in 2~7 h, e.g. 5~6 h.

In another embodiment, it was not necessary to isolate compound 3 when step (a) completed, i.e. there is no need to isolate, purify compound 3. In other words, a mixture containing compound 3 is suitable for next step, for instance, the reaction mixture from step (a), or mixture containing compound 3 by simple work-up of the reaction mixture from step (a). Simple work-up means concentration, removal of solvent, filtration etc operations. Then the mixture was carried out to next step. It preferred to be the reaction mixture from step (a) was carried out for step (d) directly. The best should be the reaction mixture from step (a) was carried out to step (b) reacting with hydrazine (better to be hydrazine hydrate) without adding any solvents.

The present invention also provided a preparation process for N-Boc biphenyl alaninol, which include following steps:
(α) Prepare compound 2 according to process described above.
(β) In methanol or/and ethanol, compound 2 react with metal borohydride to afford compound 1.

Here * indicates that compound 2 and compound 1 have chiral centers in their molecular structure. 2 and 1 have same configuration R or S.

In the above step (β) process, the ratio of methanol and/or ethanol to the mole of compound 2 was in the regular range of this kind of transformation, e.g. 1~6 L/mol; preferred to be 2~4 L/mol, e.g. 2.1~3.0 L/mol.

In the above step (β) process, the above described metal borohydride can be the common ones used in this kind of transformation. It preferred to be one of sodium borohydride, potassium borohydride and lithium borohydride, or any combination of them.

In the above step (β) process, the mole ratio of metal borohydride to compound 2 can be in the regular range used for this transformation. It preferred to be in the range of 1.0~6.0, better 2.0~4.0, e.g. 2.9~3.1.

In the above step (β) process, the reaction temperature for reduction was in the regular range of this transformation, preferred to be 0~70° C., and it better to be 15~30° C., e.g. 25~30° C.

In the above step (β) process, the completeness of the reduction can be monitored by regular methods in this area, such as TLC, HPLC or NMR. In general compound 2 stopped to react was regarded as the end point. The reaction time usually is 2~15 h, better in 4~10 h, e.g. 5~8 h.

The present invention also provided a compound 3, which is outlined as:

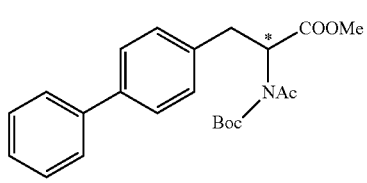

3

Here * indicates that compound 3 has chiral center in their molecular structure, which can be R or S.

In the present invention, Me stands for methyl; Ac stands for acetyl; Boc stands for tert-butyloxyl carbonyl.

Following the basic principle and art, combinations of above mentioned optimized conditions provide good examples for this invention.

All reagents and solvents used in this invention were commercial available.

The advantages of this invention are: lower cost, low cost, safe operation, less pollution and high yield. The product was obtained in >99% purity and ee which is suitable to scale up in industrial scale.

DETAILED DESCRIPTION OF THE PREFERRED EMBODIMENT

The present invention will be elucidated with reference to the following examples, without however being limited or restricted by these. If there were no detail method in any the following examples, follow regular methods and conditions.

The catalyst [Rh((Rc,Sp)-Duanphos)(NBD)]BF4 used in the example was our own product, or can be purchased from STREM.

The ee determination method in the example was: HPLC. Column: AD-H, 250×4.6 mm, 5 μm. Flow rate: 1.0 mL/min. Column temperature: 25° C. Mobile phase: n-hexane/isopropyl alcohol=85/15 (v/v). Run time: 20 min. Retention time for R: 11.6 min. S: 7.9 min.

EXAMPLE 1

3-(1, 1'-biphen-4-yl)-2-acetylaminoacrylic acid methyl ester

To a flask were added 66.4 g of 4-phenylbenzaldehyde, 85.0 g of methyl 2-acetamido-2-(dimethoxyphosphoryl)acetate and 460 mL of dichloromethane. The mixture was cooled to 0° C. and 65.0 g of DBU was added drop wise while maintaining temperature at 0~5° C. After addition, the temperature was increased to 10~25° C. and the mixture was stirred for additional 2 hours. When TLC showing no starting material, the mixture was then cooled to 10° C. The pH was adjusted to about 6~7 by adding acetic acid (~9 g). The resulting mixture was then concentrated to remove solvents under reduced pressure. To the residue was added 500 mL of water and the mixture was stirred for 1 hour. The solid was collected by filtration. The wet cake was then slurried in 500 mL of water for 1 hour. The solid was further purified by being slurried in water (500 mL, 1 h) and MTBE (500 mL, at 50° C. for 2 h). It was filtered and dried at 55° C. to afford 103 g of white solid, with HPLC purity of 99.2% in 96% yield.

$^1$H NMR (400 MHz, CDCl$_3$), δ (ppm): 7.63-7.56 (m, 6H), 7.48-7.45 (m, 2H), 7.40-7.37 (m, 1H), 7.24 (s, 1H), 3.88 (s, 3H), 2.18 (s, 3H).

EXAMPLE 2

(R)-3-(1, 1'-biphen-4-yl)-2-acetylaminopropionic acid methyl ester

To a high pressure reactor were added 15 g of 3-(1, 1'-biphen-4-yl)-2-acetylaminoacrylic acid methyl ester and 120 mL of methanol. The air in the reactor was replaced by nitrogen three times. 9 mg of catalyst Rh[(NBD)(Rc,Sp-DuanPhos)]BF4 was added under nitrogen. The reactor was charged with hydrogen and then released. Repeat this operation four times. Then the reactor was charged with hydrogen to 1.5~3 MPa and stirred at 20~30° C. for 4~8 h. When the reaction is complete monitored by HPLC, hydrogen was released carefully. The mixture was concentrated to provide 15.1 g of white solid with HPLC purity of 99.1% in 100% yield. The ee was 99.2%.

$^1$H NMR (400 MHz, CDCl3): δ=7.61~7.59 (d, 2H), 7.56~7.54 (d, 2H), 7.48~7.44 (t, 2H), 7.38~7.35 (t, 1H), 7.20~7.18 (d, 2H), 5.97~5.95 (d, 1H), 4.98~4.93 (m, 1H), 3.78 (s, 3H), 3.25~3.15 (m, 2H), 2.03 (s, 3H).

$[\alpha]D^{25}=-111.0$ (c=0.011 g/mL, CHCl$_3$).

Advanced Synthesis and Catalysis, 2013, vol. 355, 594~600 reported specific rotation of $[\alpha]D^{25}=+111.0$ (c=0.011 g/mL, CHCl$_3$) for (S)-3-(1, 1'-biphenyl-4)-2-acetylaminopropionic methyl ester. Therefor the product from this step is R configuration.

EXAMPLE 3

(R)-3-(1, 1'-biphen-4-yl)-2-tert-butoxycarbonyl-aminopropionic acid methyl ester To a flask were added 4 g of (R)-3-(1, 1'-biphen-4-yl)-2-acetylaminopropionic acid methyl ester, 0.2 g DMAP, 4.4 g (Boc)$_2$O and 28 mL of anhydrous THF. The resulting mixture was then heated to reflux (60-66° C.) for 3 hours. After the reaction was completed, it was cooled to 0~10° C. 1.9 g of hydrazine hydrate was then added and the mixture was maintained for 5 hours under 0~10° C. till HPLC showing the reaction no intermediate detected. Its pH was then adjusted to 5~6 by adding diluted hydrochloric acid. The mixture was then concentrated and the residue was dissolved in 30 mL of DCM. The organic phase was separated and washed twice with water. Concentration of the organic phase to provide light yellow solid 4.7 g with 99.3% HPLC purity and in 98% yield.

$^1$H NMR (400 MHz, CDCl$_3$): δ=7.61~7.22 (m, 9H), 5.07~5.05 (d, 1H), 4.67~4.65 (m, 1H), 3.76 (s, 3H), 3.22~3.09 (m, 2H), 1.46 (s, 9H).

$[\alpha]D^{25}=-53.0$ (c=0.01 g/mL, CHCl$_3$).

EXAMPLE 4

(R)-3-(1, 1'-biphen-4-yl)-N-Boc-alaninol

To a flask were added 25 g of (R)-3-(1, 1'-biphen-4-yl)-2-tert-butoxycarbonyl-aminopropionic acid methyl ester and 150 mL of methanol. The mixture was then cooled to 5° C. 7.7 g of sodium borohydride was then added while maintaining 5~15° C. After the addition, the mixture was heated to 25~30° C. and stirred for 5 hours till HPLC showing no starting material. Its pH was then adjusted to 7~8 by adding diluted hydrochloric acid (10%). Methanol was removed. To the residue was then added 150 mL of ethyl acetate and 100 mL of water. The mixture was then stirred well and two phases were separated. The organic phase was then washed with 5% brine, dried, concentrated to provide 21.2 g white solid with 98.7% HPLC purity in 92% yield.

$^1$H-NMR (400 MHz, CDCl$_3$): δ=7.64~7.62 (d, 2H), 7.57~7.55 (d, 2H), 7.47~7.43 (t, 2H), 7.36~7.32 (t, 1H), 7.31~7.29 (d, 2H), 6.59~6.57 (d, 1H), 4.73 (s, 1H), 3.65~3.63 (m, 1H), 3.35~3.39 (m, 1H), 2.90~2.85 (dd, 1H), 2.65~2.60 (dd, 1H), 1.37 (s, 9H).

[α]$D^{25}$=+24.1 (c=0.01 g/mL, CHCl$_3$).

US2015/210632A1 reported specific rotation of [α]$D^{25}$=+21.78 (c=0.01 g/mL, CHCl$_3$) for (R)-3-(1, 1'-biphen-4-yl)-N-Boc-alaninol. Therefor the product from this step is R configuration.

EXAMPLE 5

3-(1, 1'-biphen-4-yl)-2-acetylaminoacrylic Acid Methyl Ester

To a flask were added 3 kg of 4-phenylbenzaldehyde, 3.9 kg of methyl 2-acetamido-2-(dimethoxyphosphoryl)acetate and 20 L of dichloromethane. The mixture was cooled to 0° C. and 3 kg of DBU was added slowly while maintaining temperature at 0~5° C. After addition, the temperature was increased to 10~25° C. and the mixture was stirred for additional 4~6 hours. When HPLC showing no starting material, the mixture was then cooled to 10° C. The pH was adjusted to about 6~7 by adding acetic acid (~0.4 kg). The resulting mixture was then concentrated to remove solvents under reduced pressure. To the residue was added 23 kg of water and the mixture was stirred for 2 hour. The solid was collected by filtration. The wet cake was then slurried in 500 mL of water for 1 hour. The solid was further purified by being slurried in water (20 kg, 1 h) and MTBE (20 L, at 50° C. for 2 h). It was filtered and dried at 55° C. to afford 4.6 of white solid, with HPLC purity of 99.1% in 95% yield. The characterization data is same as that from example 1.

EXAMPLE 6

(R)-3-(1, 1'-biphen-4-yl)-2-acetylaminopropionic Acid Methyl Ester

To a high pressure reactor were added 1.8 kg of 3-(1, 1'-biphen-4-yl)-2-acetylaminoacrylic acid methyl ester and 14 L of methanol. The air in the reactor was replaced by nitrogen three times. 1.0 g of catalyst Rh[(NBD)(Rc,Sp-DuanPhos)]BF4 was added under nitrogen. The reactor was charged with hydrogen and then released. Repeat this operation four times. Then the reactor was charged with hydrogen to 1.5~3 MPa and stirred at 20~30° C. for 4~8 h. When the reaction is complete monitored by HPLC, hydrogen was released carefully. The mixture was concentrated to provide 1.8 g of white solid with HPLC purity of 99.0% in 100% yield. The ee was 99.3%. The characterization data is same as that from example 2.

EXAMPLE 7

(R)-3-(1, 1'-biphen-4-yl)-2-tert-butoxycarbonyl-aminopropionic Acid Methyl Ester To a flask were added 1.4 kg of (R)-3-(1, 1'-biphen-4-yl)-2-acetylaminopropionic acid methyl ester, 0.07 kg DMAP, 1.55 kg (Boc)$_2$O and 10 L of anhydrous THF. The resulting mixture was then heated to reflux (60-66° C.) for 5~7 hours. After the reaction was completed, it was cooled to 0~10° C. 0.67 kg of hydrazine hydrate was then added and the mixture was maintained for another 5~7 hours under 0~10° C. till HPLC showing the reaction no intermediate detected. Its pH was then adjusted to 5~6 by adding diluted hydrochloric acid. The mixture was then concentrated and the residue was dissolved in 10 L of DCM. The organic phase was separated and washed twice with water. Concentration of the organic phase to provide light yellow solid 1.57 kg with 98.5% HPLC purity and in 94% yield. The characterization data is same as that from example 3.

EXAMPLE 8

(R)-3-(1, 1'-biphen-4-yl)-N-Boc-alaninol

To a flask were added 1.5 kg of (R)-3-(1, 1'-biphen-4-yl)-2-tert-butoxycarbonyl-aminopropionic acid methyl ester and 9 L of methanol. The mixture was then cooled to 5° C. 0.5 kg of sodium borohydride was then added while maintaining 5~15° C. After the addition, the mixture was heated to 25~30° C. and stirred for 5~8 hours till HPLC showing no starting material. Its pH was then adjusted to 7~8 by adding diluted hydrochloric acid. Methanol was removed. To the residue was then added 9 L of ethyl acetate and 6 L of water. The mixture was then stirred well and two phases were separated. The organic phase was then washed with 5% saturated brine, dried, concentrated to provide 1.3 kg white solid with 98.8% HPLC purity in 94% yield. The characterization data is same as that from example 4.

What is claimed is:

1. A process for preparing compound 4, comprising (I) in an organic solvent, compound 6 condenses with compound 7 in the presence of base to afford compound 5,

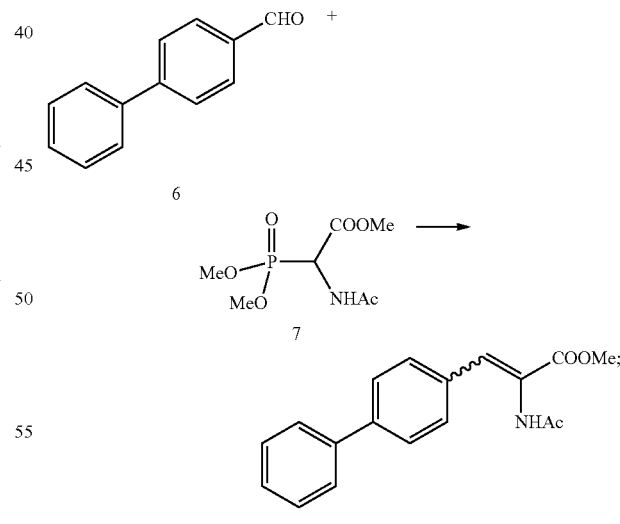

and (II) in one of the alcohol solvents, asymmetric hydrogenation of 5 in the presence of [Rh(Duanphos)(X)]Y and hydrogen to provide compound 4, wherein "Duanphos" is (Rc,Sp)-Duanphos or (Sc,Rp)-Duanphos, X is NBD or/and COD, Y is selected from the group consisting of BF4, PF6 and SbF6,

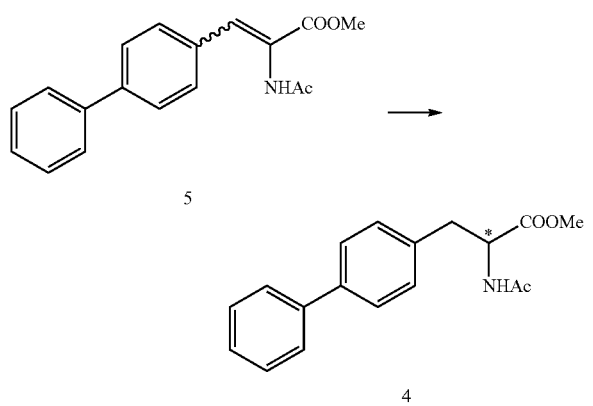

wherein, ⁓ indicates that compound 5 is E or/and Z; * indicates that compound 4 has a chiral center, which is R configuration when (Rc,Sp)-Duanphos is used, otherwise it is S configuration when (Sc,Rp)-Duanphos is used.

2. The process defined as claim 1, wherein the pressure of hydrogen is in the range of 0.1-0.5 MPa;
and/or in the process for preparing compound 4, the alcohol solvent is methanol;
and/or in the process for preparing compound 4, the ratio of the volume of the alcohol solvent to the mole of compound 5 is in the range of 1-10 L/mol;
and/or in the process for preparing compound 4, the mole ratio of [Rh(Duanphos)(X)]Y to compound 5 is in the range of 0.00001-0.01;
and/or in the process for preparing compound 4, the hydrogenation temperature is in the range of 0-60° C.;
and/or in the process for preparing compound 4, the reaction time for hydrogenation is 1-20 h.

3. The process defined as claim 2, wherein the pressure of hydrogen is in the range of 0.5-3.0 MPa;
and/or in the process for preparing compound 4, the ratio of the volume of the alcohol solvent to the mole of compound 4 is in the range of 1.5-3 L/mol;
and/or in the process for preparing compound 4, the mole ratio of [Rh(Duanphos)(X)]Y to compound 5 is in the range of 0.0001-0.0003;
and/or in the process for preparing compound 4, the hydrogenation temperature is in the range of 20-30° C.;
and/or in the process for preparing compound 4, the reaction time for hydrogenation is 4-8 h.

4. The process defined as claim 3, wherein the pressure of hydrogen is in the range of 1.5-2.0 MPa;
and/or in the process for preparing compound 4, the ratio of the alcohol solvent to the mole of compound 4 is in the range of 2.3-2.8 L/mol;
and/or in the process for preparing compound 4, the mole ratio of [Rh(Duanphos)(X)]Y to compound 5 is in the range of 0.00025-0.000265.

5. According to the process defined as claim 1, wherein in the preparation of compound 5, the reaction solvent is selected from the group consisting of haloalkanes, nitriles, alcohols, ethers and any combination thereof;
and/or in the preparation of compound 5, the ratio of the volume of the solvent to the mole of compound 7 is in the range of 1.0-3.0 L/mol;
and/or in the preparation of compound 5, the base is one of the common bases used for this transformation or any combination thereof, which is selected from the group consisting of tetramethylguanidine, sodium methoxide, sodium ethoxide, sodium hydroxide, sodium hydride, sodium amide and DBU;
and/or in the preparation of compound 5, the mole ratio of the base to compound 7 is in the range of 1.1-2.0;
and/or in the preparation of compound 5, the mole ratio of compound 6 to compound 7 is in the range of 1.0-4.0;
and/or in the preparation of compound 5, the reaction temperature for condensation is in the range of 0-40° C.;
and/or in the preparation of compound 5, the reaction time for condensation is 2-8 h.

6. The process defined as claim 5, wherein in the preparation of compound 5, the haloalkane solvent is dichloromethane;
and/or, in the preparation of compound 5, the nitrile solvent is acetonitrile;
and/or, in the preparation of compound 5, the alcohol solvent is methanol and/or ethanol;
and/or, in the preparation of compound 5, the ether solvent is methyl tent-butyl ether;
and/or, in the preparation of compound 5, the ratio of the volume of the solvent to the mole of compound 7 is in the range of 1.3-1.6 L/mol;
and/or, in the preparation of compound 5, the base is DBU;
and/or, in the preparation of compound 5, the mole ratio of the base to compound 7 is in the range of 1.2-1.6;
and/or, in the preparation of compound 5, the mole ratio of compound 6 to compound 7 is in the range of 1.1-2.0;
and/or, in the preparation of compound 5, the reaction temperature for condensation is in the range of 10-25° C.;
and/or, in the preparation of compound 5, the reaction time for condensation is 4-6 h.

7. A process for preparing compound 3, which comprises:
(1) preparing compound 4 according
a process comprising in one of the alcohol solvents, asymmetric hydrogenation of 5 in the presence of [Rh(Duanphos)(X)]Y and hydrogen to provide compound 4, wherein "Duanphos" is (Rc,Sp)-Duanphos or (Sc,Rp)-Duanphos, X is NBD or/and COD, Y is selected from the group consisting of BF4, PF6 and SbF6,

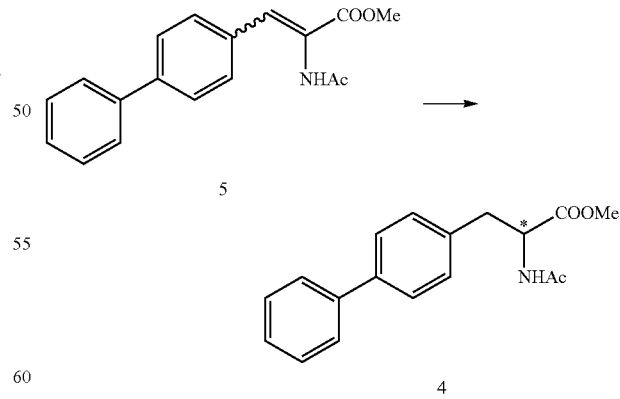

wherein, ⁓ indicates that compound 5 is E or/and Z; * indicates that compound 4 has a chiral center, which is R configuration when (Rc,Sp)-Duanphos is used, otherwise it is S configuration when (Sc,Rp)-Duanphos is used;

(2) in the presence of a base, reacting compound 4 with di-tert butyl dicarbonate to form compound 3;

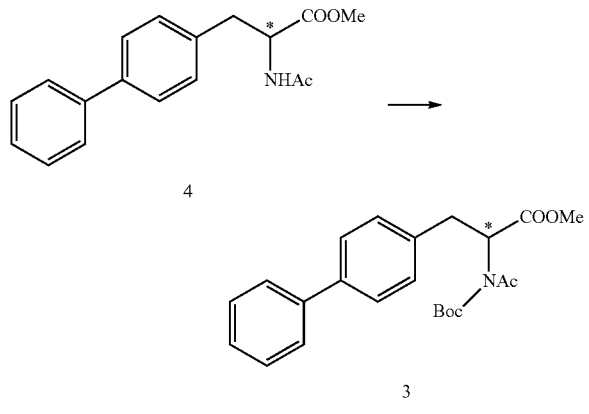

wherein, * indicates that compound 4 and compound 3 have chiral centers in their molecular structure, and compound 4 and compound 3 have same configuration R or S.

8. The process defined as claim 7, wherein in step (2), a reaction solvent is selected from the group consisting of haloalkanes, nitriles, alcohols, ethers, pyridine, NMP and any combination thereof;
and/or, in step (2), the ratio of the volume of the solvent to the mole of compound 4 is in the range of 1-6 L/mol;
and/or, in step (2), the base is an inorganic base and/or an organic base;
and/or, in step (2), the mole ratio of the base to compound 4 is in the range of 0.1-0.2;
and/or, in step (2), the mole ratio of di-tent butyl dicarbonate to compound 4 is in the range of 1.2-2.0;
and/or, in step (2), the reaction temperature for bocylation is in the range of 30-70° C.;
and/or, in step (2), the reaction time for bocylation is 3-7 h.

9. The process defined as claim 8, wherein in step (2), the haloalkane solvent is dichloromethane;
and/or, in step (2), the nitrile solvent is acetonitrile;
and/or, in step (2), the alcohol solvent is methanol;
and/or, in step (2), the ether solvent is tetrahydrofuran;
and/or, in step (2), the ratio of the volume of the organic solvent to the mole of compound 4 is in the range of 2-3 L/mol;
and/or, in step (2), the inorganic base is sodium bicarbonate and/or sodium carbonate;
and/or, in step (2), the organic base is selected from the group consisting of ammonia aqueous, morpholine, pyridine, triethyl amine, ethanol amine, ethylene diamine, 4-dimethylaminopyridine, diisopropyl ethyl amine and any combination thereof;
and/or, in step (2), the mole ratio of the base to compound 4 is in the range of 0.12-0.18;
and/or, in step (2), the mole ratio of di-tent butyl dicarbonate to compound 4 is in the range of 1.5-1.8;
and/or, in step (2), the reaction temperature for bocylation is in the range of 60-66° C.;
and/or, in step (2), the reaction time for bocylation is 5-6 h.

10. A process for preparing compound 2, which comprises:

(a) preparing compound 3 according to the process defined as claim 7;
(b) in an organic solvent, reacting compound 3 with hydrazine to afford compound 2;

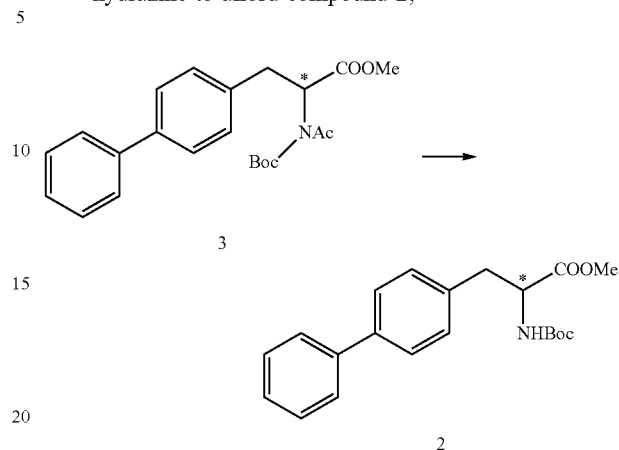

wherein * indicates that compound 3 and compound 2 have chiral centers in their molecular structure and compound 3 and compound 2 have same configuration R or S.

11. The process defined as claim 10, wherein in step (b), the organic solvent is selected from the group consisting of haloalkanes, nitriles, alcohols, ethers, pyridine and NMP and any combination thereof;
and/or, in step (b), the ratio of the volume of the solvent to the mole of compound 3 is in the range of 1-6 L/mol;
and/or, in step (b) which is hydrazinolysis, the hydrazine is added in the form of hydrazine hydrate;
and/or, in step (b) which is hydrazinolysis, the mole ratio of hydrazine to compound 3 is in the range of 2-4;
and/or, in step (b), the reaction temperature for hydrazinolysis is in the range of 0-20° C.;
and/or, in step (b), the reaction time for hydrazinolysis is 2-7 h.

12. The process defined as claim 11, wherein in step (b), the haloalkane solvent is dichloromethane;
and/or, in step (b), the nitrile solvent is acetonitrile;
and/or, in step (b), the alcohol solvent is methanol;
and/or, in step (b), the ether solvent is tetrahydrofuran;
and/or, in step (b), the ratio of the volume of the solvent to the mole of compound 3 is in the range of 2-3 L/mol;
and/or, in step (b) which is hydrazinolysis, the mole ratio of hydrazine to compound 3 is in the range of 2.8-3.5;
and/or, in step (b), the reaction temperature for hydrazinolysis is in the range of 0-10° C.;
and/or, in step (b), the reaction time for hydrazinolysis is 5-6 h.

13. The process defined as claim 10, wherein compound 3 is not necessary to be isolated when step (a) is completed, which means there is no need to isolate and purify compound 3, which is used directly for step (b).

14. A process for preparing N-Boc biphenyl alaninol, which comprises:

(a) preparing compound 2 according to the process defined as claim 10;
(b) in methanol or/and ethanol, reacting compound 2 with metal borohydride to afford compound 1;

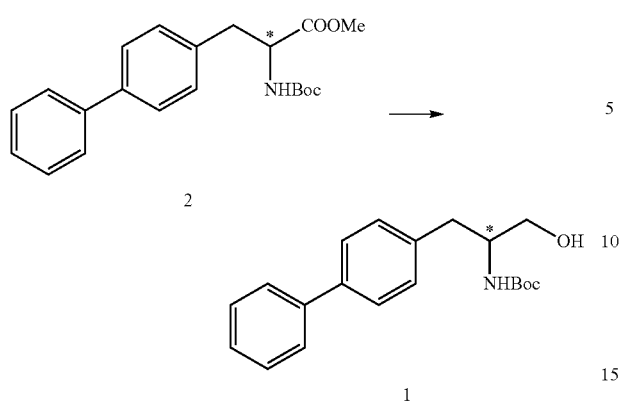

wherein, * indicates that compound 2 and compound 1 have chiral centers in their molecular structure, and compound 2 and compound 1 have same configuration R or S.

15. The process defined as claim 14, wherein in step (b) of preparing compound 1, the ratio of the volume of methanol and/or ethanol to the mole of compound 2 is in the range of 2-4 L/mol;

and/or, in step (b) of preparing compound 1, the metal borohydride is selected from the group consisting of sodium borohydride, potassium borohydride, lithium borohydride, and any combination thereof;

and/or, in step (b) of preparing compound 1, the mole ratio of metal borohydride to compound 2 is in the range of 2.0-4.0;

and/or, in step (b) of preparing compound 1, the reaction temperature for reduction is 15-30° C.;

and/or, in step (b) of preparing compound 1, the reaction time for reduction is 4-10 h.

16. The process defined as claim 15, wherein in step (b) of preparing compound 1, the ratio of the volume of methanol and/or ethanol to the mole of compound 2 is in the range of 2.1-3.0 L/mol;

and/or, in step (b) of preparing compound 1, the metal borohydride is sodium borohydride;

and/or, in step (b) of preparing compound 1, the mole ratio of metal borohydride to compound 2 is in the range of 2.9-3.1;

and/or, in step (b) of preparing compound 1, the reaction temperature for reduction is 25-30° C.;

and/or, in step (b) of preparing compound 1, the reaction time for reduction is 5-8 h.

17. Compound 3, which is represented as:

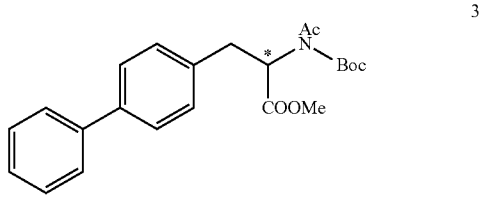

wherein, * indicates that compound 3 has chiral center in their molecular structure, which is R or S.

* * * * *